US007118562B2

(12) United States Patent
Furumoto

(10) Patent No.: US 7,118,562 B2
(45) Date of Patent: *Oct. 10, 2006

(54) LASER SYSTEM AND METHOD FOR TREATMENT OF BIOLOGIC TARGETS

(75) Inventor: Horace W. Furumoto, Wellesley, MA (US)

(73) Assignee: Cynosure, Inc., Westford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/631,213

(22) Filed: Jul. 31, 2003

(65) Prior Publication Data

US 2004/0024390 A1 Feb. 5, 2004

Related U.S. Application Data

(63) Continuation of application No. 09/925,589, filed on Aug. 9, 2001, now Pat. No. 6,610,052, which is a continuation of application No. 08/835,012, filed on Apr. 8, 1997, now Pat. No. 6,273,883, which is a continuation of application No. PCT/US97/05560, filed on Apr. 4, 1997, said application No. 08/835,012 is a continuation of application No. 08/745,133, filed on Nov. 7, 1996, now Pat. No. 5,843,072, and a continuation of application No. 08/744,344, filed on Nov. 7, 1996, now Pat. No. 5,871,479.

(60) Provisional application No. 60/015,082, filed on Apr. 9, 1996.

(51) Int. Cl.
*A61B 18/18* (2006.01)
*A61B 18/20* (2006.01)

(52) U.S. Cl. .............................. 606/9; 606/3; 128/898

(58) Field of Classification Search .................... 606/3, 606/7–10; 128/898
See application file for complete search history.

(56) References Cited

U.S. PATENT DOCUMENTS

| 3,693,623 A | 9/1972 | Harte et al. |
| 3,914,709 A | 10/1975 | Pike et al. |
| 4,489,415 A | 12/1984 | Jones, Jr. |
| 4,555,786 A | 11/1985 | Byer |
| 4,656,641 A | 4/1987 | Scifres et al. |

(Continued)

FOREIGN PATENT DOCUMENTS

DE 3841 503 A1 6/1990

(Continued)

OTHER PUBLICATIONS

"*Variable Pulsewidth Laser Controller*," Model 8800V, Analog Modules, Inc., 126 Baywood Ave., Longwood, Florida 32750-3426, Advertisement (May 1995).

(Continued)

*Primary Examiner*—A. Farah
(74) *Attorney, Agent, or Firm*—Hamilton, Brook, Smith & Reynolds, P.C.

(57) ABSTRACT

A long pulse alexandrite laser for treating dermatological specimens is disclosed. The use of alexandrite allows operation in the near-infrared, specifically in a 50 nm range surrounding 755. Infrared in this range allows good penetration while still achieving an acceptable ratio of hemoglobin to melanin absorption In addition, a method and related system for treating biologic tissue with pulse light includes generating a long effective output light pulse comprising a series of sub-pulses having a fractional duty cycle over a selected effective pulse duration, a periodicity that is less than the thermal relaxation time of a targeted structure, and an interpulse-delay between successive sub-pulses that is greater than the thermal relaxation time of non-targeted structures within the treatment area; and delivering the output light to the tissue of a patient.

10 Claims, 6 Drawing Sheets

U.S. PATENT DOCUMENTS

| | | | |
|---|---|---|---|
| 4,862,888 | A | 9/1989 | Yessik |
| 4,901,323 | A | 2/1990 | Hawkins et al. |
| 5,066,293 | A | 11/1991 | Furumoto |
| 5,071,416 | A | 12/1991 | Heller et al. |
| 5,090,019 | A | 2/1992 | Scheps |
| 5,255,277 | A | 10/1993 | Carvalho |
| 5,312,396 | A | 5/1994 | Feld et al. |
| 5,344,418 | A | 9/1994 | Ghaffari |
| 5,387,211 | A | 2/1995 | Saadatmanesh et al. |
| 5,405,368 | A | 4/1995 | Eckhouse |
| 5,423,800 | A | 6/1995 | Ren et al. |
| 5,488,626 | A | 1/1996 | Heller et al. |
| 5,541,948 | A | 7/1996 | Krupke et al. |
| 5,558,667 | A | 9/1996 | Yarborough et al. |
| 5,595,568 | A | 1/1997 | Anderson et al. |
| 5,658,323 | A | 8/1997 | Miller |
| 5,735,844 | A | 4/1998 | Anderson et al. |
| 5,749,868 | A | 5/1998 | Furumoto |
| 5,868,732 | A | 2/1999 | Waldman et al. |
| 5,879,346 | A | 3/1999 | Waldman et al. |
| 5,879,376 | A | 3/1999 | Miller |
| 5,897,549 | A | 4/1999 | Tankovick |
| 5,964,749 | A * | 10/1999 | Eckhouse et al. .............. 606/9 |
| 6,027,495 | A * | 2/2000 | Miller .......................... 606/9 |
| 6,050,990 | A | 4/2000 | Tankovich et al. |
| 6,142,939 | A | 11/2000 | Eppstein et al. |
| 6,197,020 | B1 * | 3/2001 | O'Donnell, Jr. ............... 606/9 |
| 6,210,426 | B1 | 4/2001 | Cho et al. |
| 6,228,074 | B1 | 5/2001 | Almeida |
| 6,273,883 | B1 | 8/2001 | Furumoto |
| 6,364,872 | B1 * | 4/2002 | Hsia et al. ..................... 606/9 |
| 6,610,052 | B1 * | 8/2003 | Furumoto ...................... 606/9 |

FOREIGN PATENT DOCUMENTS

| | | |
|---|---|---|
| DE | 3841503 A1 | 6/1990 |
| EP | 0 142 671 A1 | 5/1985 |
| EP | 0 458 576 A2 | 11/1991 |
| EP | 0 575 274 A1 | 12/1993 |
| JP | HO 62-165985 | 7/1987 |
| JP | 4-6389 | 1/1992 |
| WO | 91/12050 | 8/1991 |
| WO | WO 91/12050 | 8/1991 |
| WO | WO 92/03977 | 3/1992 |
| WO | 95/335518 | 12/1995 |
| WO | 96/23447 | 8/1996 |
| WO | 97/37602 | 10/1997 |

OTHER PUBLICATIONS

"*A Practical Guide for the PhotoDern® VL user*," Energy Systems Corporation, Oct. 1995.

* cited by examiner

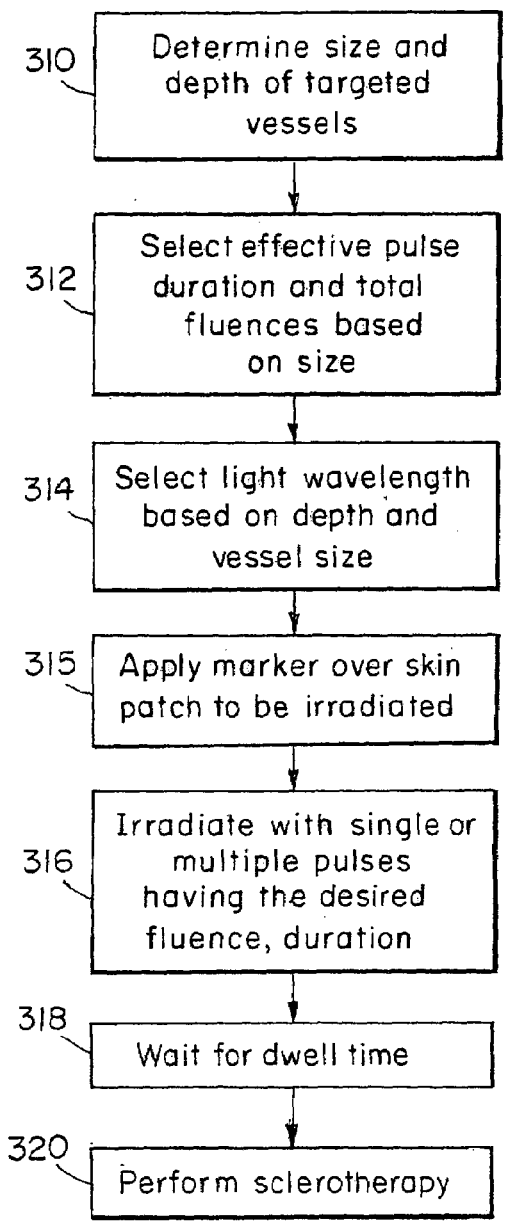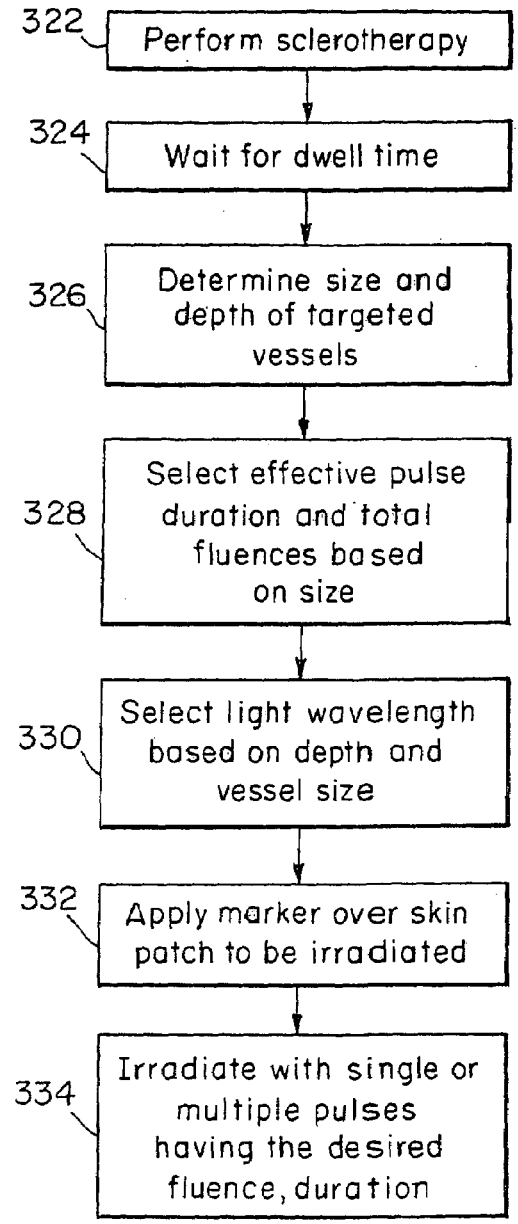
FIG. 7A
FIG. 7B

LASER SYSTEM AND METHOD FOR TREATMENT OF BIOLOGIC TARGETS

RELATED APPLICATIONS

This application is a continuation of U.S. patent application Ser. No. 09/925,589, filed Aug. 9, 2001, now U.S. Pat. No. 6,610,052 which is a continuation of U.S. patent application Ser. No. 08/835,012, filed Apr. 8, 1997, now U.S. Pat. No. 6,273,883 entitled "Alexandrite Laser System for Treatment of Dermatological Specimens," by Horace W. Furumoto, et al., which is a continuation of International Application No. PCT/US97/05560, filed Apr. 4, 1997, which claims the benefit of U.S. Provisional Patent Application Ser. No. 60/015,082, filed Apr. 9, 1996, the teachings of which are incorporated herein by this reference in their entirety. U.S. patent application Ser. No. 08/835,012 is also a continuation of U.S. patent application Ser. No. 08/745,133, filed Nov. 7, 1996, now U.S. Pat. No. 5,843,072 the teachings of which are incorporated herein by this reference in their entirety, and a continuation of U.S. patent application Ser. No. 08/744,344, filed Nov. 7, 1996, now U.S. Pat. No. 5,871,479 the teachings of which are incorporated herein by this reference in their entirety.

BACKGROUND OF THE INVENTION

The principle of selective photothermolysis underlies many laser therapies and is used to treat such diverse dermatological problems as leg veins, portwine stain birthmarks, other ectatic vascular lesions, and pigmented lesions including tattoos. The dermal and epidermal layers containing the targeted structures are irradiated with light, usually from lasers or flashlamps. The wavelength or color of this light is chosen so that its energy will be preferentially or selectively absorbed in the structures. This leads to the localized heating with the intent of raising the temperature to a point at which constituent proteins will denature or pigment particles will disperse.

The pulse duration of the irradiating light is also important for selectivity. If the pulse duration is too long, heat absorbed by the structures will diffuse out into the surrounding tissues and will not be selectively heated to the degree necessary. If the pulse durations are too short, however, the light absorbing chemical species such as blood hemoglobin or tattoo dye particle will be heated too quickly causing vaporization. Theory dictates that the proper pulse width should match the thermal diffusion time of the targeted structures. For smaller vessels contained in portwine stain birthmarks, for example, these thermal diffusion times can be on the order of hundreds of microseconds (μsec) to several milliseconds (msec). Larger leg veins have thermal diffusion times in the 5 to 100 msec range. Pigmented lesion particles can have diffusion times as short as nanoseconds (nsec).

Various types of lasers have been tested for selective photothermolysis in dermatological specimens. Q-switched alexandrite lasers have been successfully used to treat naturally occurring dermatological pigmentations and also tattoos. Long-pulsed ruby lasers have been proposed for the removal of hair. Nd:YAG lasers (operating at 1060 nm), carbon dioxide (operating at 10.6 micrometers), and argon (operating in the 488–514 nm range) have been suggested for the treatment of ectatic vessels. The most successful vascular treatments have been achieved using dye lasers, and specifically flashlamp-excited pulse dye lasers. These lasers operate in the 577–585 nm range where there are absorption band peaks for hemoglobin and also operate well in the pulsed mode that provides for good selectivity. With the proper selection of color and pulse duration, success rates of higher than 50% are common when treating smaller vessels. Unfortunately, dye lasers are limited in pulse durations to less than 1.5 milliseconds. Thus, they tend to be inappropriate for the treatment of larger structures that would require pulse durations of hundreds of milliseconds, at least according to the principle. Attempts are being made to solve this problem. Frequency doubling Nd:YAG has been proposed as a technique to generate long pulses at 532 nm.

SUMMARY OF THE INVENTION

The present invention is directed to a long pulse alexandrite laser for treating dermatological specimens. The use of alexandrite allows operation in the near-infrared, specifically in a 100 nm range surrounding 760 nm where alexandrite is tunable, and ideally at approximately 755 nm and a surrounding 50 nm range±25 nm. Infrared in this range penetrates well while still achieving an acceptable ratio of hemoglobin to melanin absorption. Moreover, the use of a long pulse alexandrite laser, in contrast to short-pulse, Q-switched versions of the laser typically used on pigmented lesions and tattoos, yields two advantages: 1) the pulse duration now can match the thermal relaxation times of larger dermatological structures; and 2) the removal of the Q-switching element makes a laser system that is less temperamental and easier to operate.

Ideally, the laser generates a laser light output pulse having a duration between 5 and 100 msec, with an output up to 50 Joules and with a delivered fluence, Joules per square centimeter ($J/cm^2$), between 10 and 50 $J/cm^2$. Spot sizes between from 0.1 to 10 $cm^2$ are preferred for efficient coverage of the targeted area. A light delivery system is provided that transmits the laser light output pulse to dermatological targets of a patient.

In specific embodiments, the pulse is comprised of multiple resonant modes, which are supported by a hemispherical resonator configuration. Preferably, a radius of curvature of at least one of the resonator mirrors is shorter than a focal length of a thermal lens induced in the alexandrite gain media during generation of the laser light output pulse. This desensitizes the laser to this lens.

In other aspects of the embodiments, an active pulse forming network is used to drive at least one flashlamp to pump the alexandrite, the network allows pulse periodic heating to achieve the effect of longer pulse durations. These pulse periodic principles, however, may be generalized to other types of flashlamp excited lasers In general, the pulse periodic heating techniques may also be applied to other types of flashlamp-excited lasers, such as dye and ruby, as a way of efficiently generating effectively long pulses of limited fluences as required in selective photothermolysis applications, for example. In addition, pulse periodic heating may also be employed in other solid-state lasers, as well as gas-discharge lasers. These techniques rely on the use of a series of laser light pulses with a limited duty cycle that have a total duration of the thermal relaxation time of the targeted structure, blood vessels for example. The total power of the pulses is that necessary to denature the targeted vessels. The pulse periodic heating technique efficiently uses the laser by reducing the energy absorbed by the gain media to get to the laser threshold. This energy does not contribute to laser action and is lost. Most commonly, pulse periodic heating is useful in dermatological applications for flashlamp-excited laser that require pulses of 10 msec and longer. Numerous other effective pulse durations may be achieved, including effective pulse durations greater than 0.1, 0.5, 5, or 50 msec.

The present invention is also directed to a long pulse alexandrite laser hair removal system. The use of an alexandrite in the present invention allows operation in the near-infrared, which provides good penetration to the hair root while still achieving an acceptable ratio of hemoglobin to melanin absorption.

In specific embodiments, it is desirable to use an index-matching application on the skin sections to be treated. This substance covers the epidermal layer to provide better coupling of the laser light into the skin.

In other aspects of the embodiments, a topical indicator is also preferably used on the skin. Skin irradiation in the near-infrared generally does not produce any characteristic skin color change as is found when using dye pulsed lasers, for example. Thus, it is difficult to know exactly what portions of the skin have already been irradiated during a treatment session. The visual indicator is thermo- or photo-responsive or otherwise responsive to the laser light pulse to generate a visible change. This provides the operator with a record of those parts of the skin that have already been treated.

The skin is preferably treated with laser pulses of greater than a millisecond, preferably approximately 5 to 50 msec. Each pulse should contain a fluence of between 10 and 50 $J/cm^2$. During each treatment session, each treated section of the skin is preferably irradiated with one such pulse, although multiple pulses could be used. Even so, permanent and complete laser removal may require three to four repeat treatment sessions, with weeks to months long dwell times between each session.

The present invention is also directed to a combined sclerotherapy and light treatment method for the cosmetic, i.e., non-therapeutic, treatment of unwanted veins. It is similar to flamplamp-excited pulse dye laser-sclerotherapy approaches from the prior art. Substantially increased success, in the range of 90–100%, however, has been achieved by implementing a dwell time of between 12 hours and 6 months between the light-based therapy and the sclerotherapy. Preferably, the light-based therapy is performed before the sclerotherapy. Success can be achieved by performing the sclerotherapy followed by the light-based therapy after the dwell time, however.

In specific embodiments, an alexandrite laser operating in the 755 nanometer range is a preferred light source, although flashlamp sources could also be used.

According to another aspect, the invention also features a kit for the treatment of unwanted blood vessels. It comprises a light source for irradiating the vessels with light adapted to initiate destruction of the vessels. A sclerosing agent, such as a hypertonic saline solution, is also needed for injection into the vessels. Instructions are desirably provided with the light source that suggest waiting for a dwell time between the irradiation of the vessels and sclerosing agent injection.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 7A and 7B are process diagrams illustrating combined light and sclerotherapy techniques for treating leg veins according to the two embodiments of the present invention;

DETAILED DESCRIPTION OF THE PREFERRED EMBODIMENTS

Figure 1:
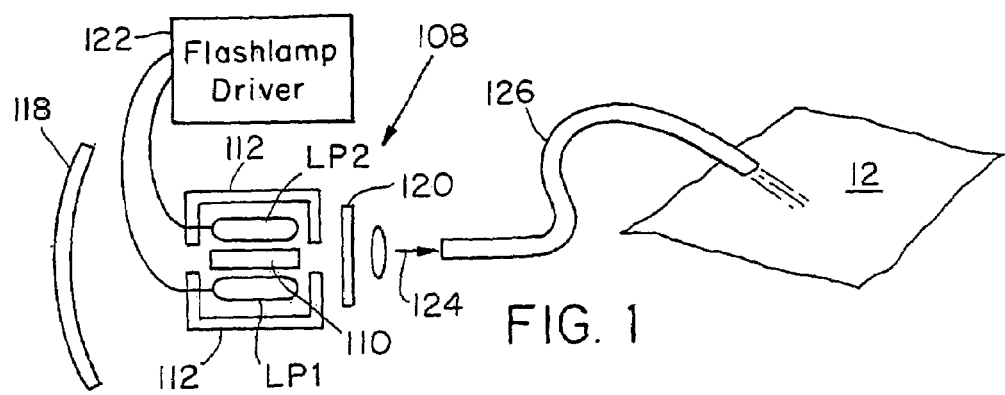
FIG. 1 is a schematic view of the inventive alexandrite laser system illustrating its use for the treatment of dermatological specimens.

FIG. 1 shows an alexandrite laser system, which has been constructed according to the principles of the present invention. An alexandrite laser 108 generally comprises one or more flashlamps LP1 and LP2 that are disposed around a usually centrally located alexandrite crystal gain medium 110. The flashlamps LP1, LP2 irradiate the gain medium either directly or via the associated reflectors 112. The flashlamps LP1, LP2 are driven by a flashlamp driver 122.

The use of the alexandrite laser is preferred to other laser systems for a number of reasons. Pulsed dye lasers operating in the 577–585 nm range are well absorbed by the deoxy-hemoglobin (Hb) and oxy-hemoglobin ($HbO_2$) relative to the melanin. This provides good selectivity. The problem, however, is that the total absorption of the melanin is very high. As a result, the laser light does not penetrate very deeply into the dermal layer. To effectively reach some dermal structures, the light must penetrate deeply, up to 5 millimeters.

Ruby lasers operating at 694 nm do achieve good penetration since the absorption of melanin is incremently lower at this wavelength. The problem here, however, is that the Hb and $HbO_2$ have low absorptions at this wavelength.

In contrast, in the 50 nm range surrounding 755 nm, where the inventive alexandrite laser system operates, melanin absorption is lower, compared to the ruby laser. Thus, better penetration is achieved. Somewhat more importantly, however, is the fact that the absorption of Hb peaks in this range and the absorption of $HbO_2$ is substantially higher than at the ruby laser's wavelength.

The use of the alexandrite laser has further, more utilitarian, advantages. Long pulse dye and ruby lasers tend to be inefficient and thus large devices. Moreover, pulsed dye lasers have the added drawback of requiring the dye gain media, which are not efficient in the infrared. In contrast, long pulse alexandrite laser systems are substantially smaller, and the conversion of energy from the flashlamps into the output laser light pulse is much more efficient than either dye or ruby lasers.

A still further advantage relative to dye lasers is the fact that alexandrite lasers generally allow longer pulse durations than dye lasers allowing treatment of larger dermal structures.

Use of the long pulse alexandrite laser 108 also has certain advantages relative to other alexandrite laser systems used in the prior art for tattoo removal and pigmented lesion treatment. Historically, alexandrite lasers generally have been viewed as difficult to implement. The Q-switching element in the laser cavity made operation of the laser unstable. In the present laser system 108, the Q-switching element is removed and the gain medium laser is driven into the longer pulse durations. This improves the operation of the laser.

The alexandrite crystal 110 generates a laser light output pulse 124 in the laser's resonant cavity, which is defined by mirrors 118 and 120. Mirror 120 is only partially reflecting and thus provides the laser's output aperture. The reflectance of the output aperture mirror 120, however, is relatively high. Generally, in Q-switched lasers, the reflectance of the output aperture mirror will be less than or equal to 50%. This is due to the fact that high peak pulse powers are to be generated, but only for a short pulse duration. In contrast, in the present long pulse alexandrite laser system, the driving factor is to increase the laser's efficiency when operating just above the laser's pumping threshold. As a result, the reflectance of mirror 120 in the present invention is preferably greater than or equal to 70%, 80% in one embodiment.

In the preferred embodiment, the resonator cavity defined by mirrors 118 and 120 is near-hemispheric. In this configuration, the output reflector 120 is a plane or near-planar mirror and the total reflecting mirror 118 is curved. Preferably, its radius of curvature is between 0.5 and 1 meters.

The radius of curvature of mirror 118 in the preferred hemispheric resonator embodiment or the combined radii of curvature for the mirrors in an alternative more concentric cavity configuration is preferably short to compensate for thermal lensing in the alexandrite crystal 110. Thermal lensing is created in the laser rod 110 because of temperature gradients. By necessity, the alexandrite crystal 110 is cooled at its periphery by conventional techniques. The absorbed heat that is not converted to laser output must be extracted by flowing, cooling liquid or gas around the crystal 110. It can be inferred that the crystal's longitudinal central axis has the highest temperatures because a temperature gradient is necessary to extract heat. The temperature gradient causes a thermal lens to form, and since most materials have a positive temperature coefficient of thermal expansion, the lens is positive. In general, a laser resonator can be designed to compensate for any power added to the resonator by thermal lensing. The problem arises when the lensing is a variable as in the case when lasers are excited at different powers to extract different outputs. Because of this, most commercial lasers are activated at constant average power and variable output is obtained by other means such as with absorptive or reflective attenuators.

Special problems, however, arise when extra-long pulse durations are needed, such as in treating leg veins and hair follicles or other larger dermatological structures using photothermolysis principles. The pulse durations needed are between 1 and 100 msec, and generally greater than 5 msec.

The alexandrite crystal can form a thermal lens while the crystal is lasing. This dynamic lensing can not be corrected with static optical elements.

In the present invention, the effect of the dynamic lensing is minimized by selecting the resonator optics. Specifically, the power of the mirrors 118, 120 is selected to be much greater than the thermal lens power induced in the alexandrite crystal by heating during the pulse. This concept is, of course, also effective on thermal lensing correction between pulses.

In the present invention, the radius of at least one of the resonator mirrors, in the illustrated embodiment lens 118, should have a high curvature with a focal length much shorter than the focal length of the induced thermal lens. Thermal lensing can add a power of as much as one diopter to the cavity, and to minimize the effect of the thermal lens, the resonator mirror 118 should have a significant power. In one embodiment, the 0.5 meter radius resonator mirror will have a focal length of 4 diopters and any thermal lensing of up to one diopter will have reduced effects on the resonator. By comparison, conventional resonator mirrors have curvatures of several meters.

Another design factor is the length of the resonant cavity as defined by mirrors 118 and 120. In the preferred embodiment, the cavity is relatively short, 15 inches or approximately 38 centimeters. The hemispheric laser resonant cavity can become unstable when the thermal lens factor is added. Thus, the intercavity spacing between mirrors 118 and 120 should be shorter than the mirror curvature by the contribution of the thermal lens.

A short radius of curvature and a short resonator will affect the Fresnel number of the cavity. The Fresnel number is $\alpha^2/\lambda D$, where $\alpha$ is the waist radius, $\lambda$ the wavelength, and $D$ the mirror separation. For lowest order mode laser, the Fresnel number must be equal to or less than unity, and free space lasers are designed using this criterion. When beam divergence is not of significance, a multimode laser can be considered and the Fresnel number can be significantly larger than unity. In fact, if a highly uniform top hat beam profile is desired, the more modes, the better. In our example, using a inter-mirror spacing of 0.4 meters, nearly equal to the mirror curvature, and using the cross section of the rod to simulate a "waist" (a waist is not definable in a highly multimode laser), we get an effective Fresnel number of:

$$F = \alpha^2/\lambda D$$

$$\alpha \simeq 3 \text{ mm for } 1/4'' \text{ diameter}$$

$$\lambda = 0.755 \text{ micron}$$

$$D = 0.4 \text{ meters}$$

$$F = \frac{\alpha^2}{\lambda D} = \frac{(3 \times 10^{-3})^2}{.755 \times 10^{-6} \times 0.4} \simeq 30$$

which leads to a very multimode laser.

The design of a laser system for surface treatment, such as those encountered in dermatology and plastic surgery treatments is based on principles different from those used in optimizing free space lasers generally. In a free space laser system, the intent is to generate lower order modes and preferably the lowest order $TEM_{00}$ mode. The characteristics of a $TEM_{00}$ laser are well understood, and the Gaussian spatial beam profiles in the near and far field are readily analyzable. The $TEM_{00}$ mode can be propagated over long distances under classic laser conditions. For surface treatment, however, it is not necessary to have a long depth of field inherent in low order mode lasers. Surfaces by definition are the outside boundary of a target and any interaction of the laser field with the target occurs over a short interaction depth. The interaction is in the form of absorption or scattering. The important parameter in surface interactions is intensity on the surface, rather than irradiance, which includes beam divergence. In more easily understood terms, the beam divergence of the incoming radiation field at the surfaces is of little consequence in surface interactions, especially if the surface is highly absorbing and scattering such as in epidermal and dermal skin layers. Thus, the multimode characteristic is acceptable when heating dermal specimens.

The pulse from the cavity is preferably coupled into a medical delivery system 126, which can take any one of a number of different forms including fiber optics. In the illustrated example, it is a fiber optic light guide that transmits the pulse from the laser to the dermal specimen that is to be treated. Specifically, a quartz fiber delivery system can be used. The longer pulses that are characteristic of the present invention allow the use of the quartz. Although relatively high energies are generated with the laser light output pulse 124, 20–40 J, the low peak powers avoid damage to the delivery system.

One problem that arises with the use of a highly multimode laser is the fact that the resulting beam is difficult to propagate using low f number optics. Optical fibers having diameters of up to 1.5 mm core diameter with numerical apertures that can accept the focusing of the highly divergent beams from the laser are commercially available.

The use of fiber, in addition to its convenience and low cost compared with articulated arms, has other advantages. A laser operating at low excitation level, often will lase only on the periphery, creating an annular output profile. With an articulated arm, this image is transferred to the target. A fiber delivery system will homogenize such a beam and produce the desired uniform top hat profile at the output aperture.

Figure 2B:
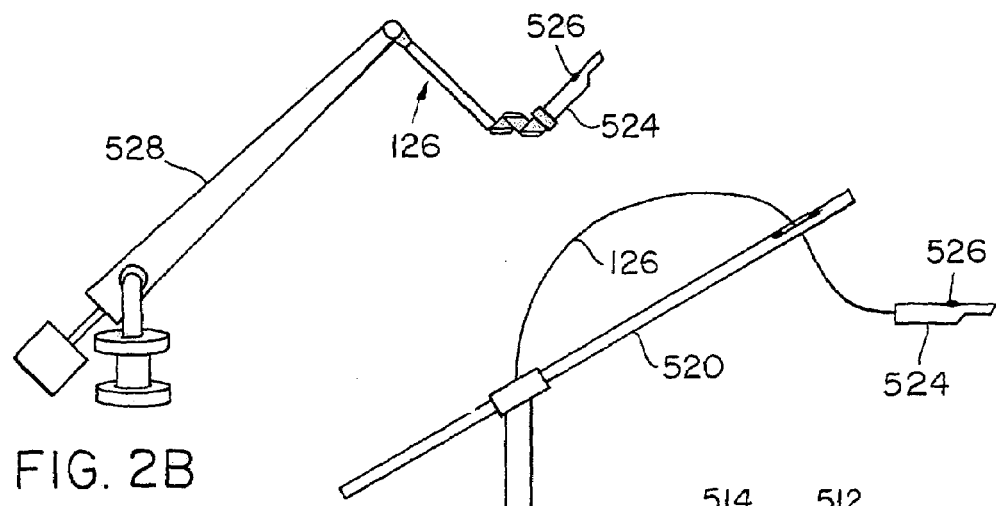
FIGS. 2A and 2B are schematic views of two embodiments of the alexandrite laser system.
Figure 2A:
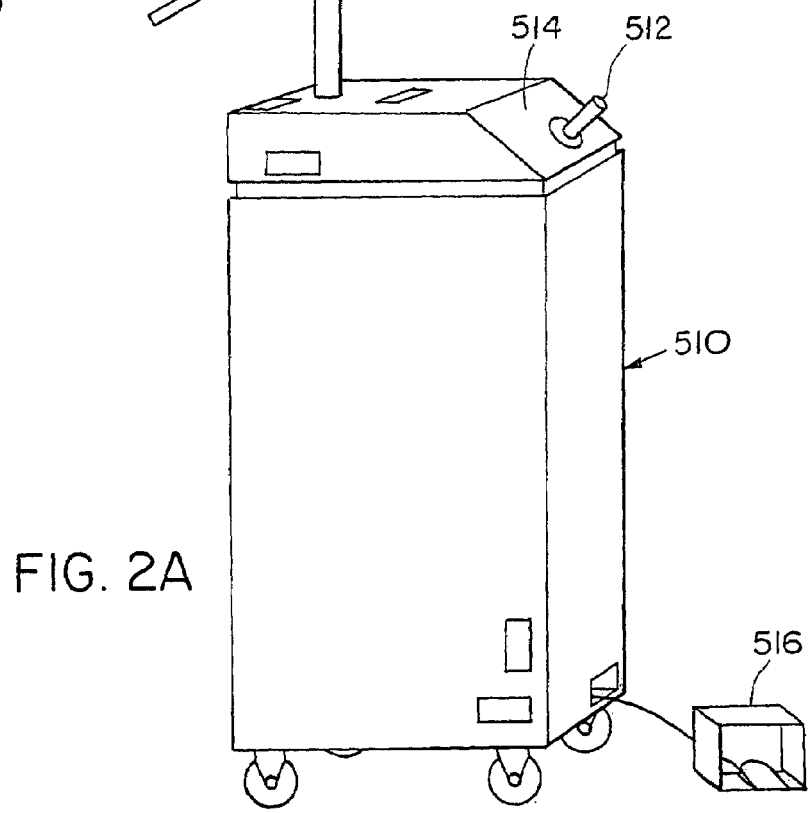

FIGS. 2A and 2B show two implementations of the laser system that would be appropriate for in-office treatment. They comprise a main unit 510 that has a calibration port 512 and a front control panel 514. A foot switch 516 is provided for convenient control. A swing arm 520 holds the optical delivery fiber 126 that ends in a handpiece 524. The handpiece has a finger switch 526 also for activation. FIG. 2B shows another embodiment using an articulated arm 528 as the delivery system 126.

Figure 3:
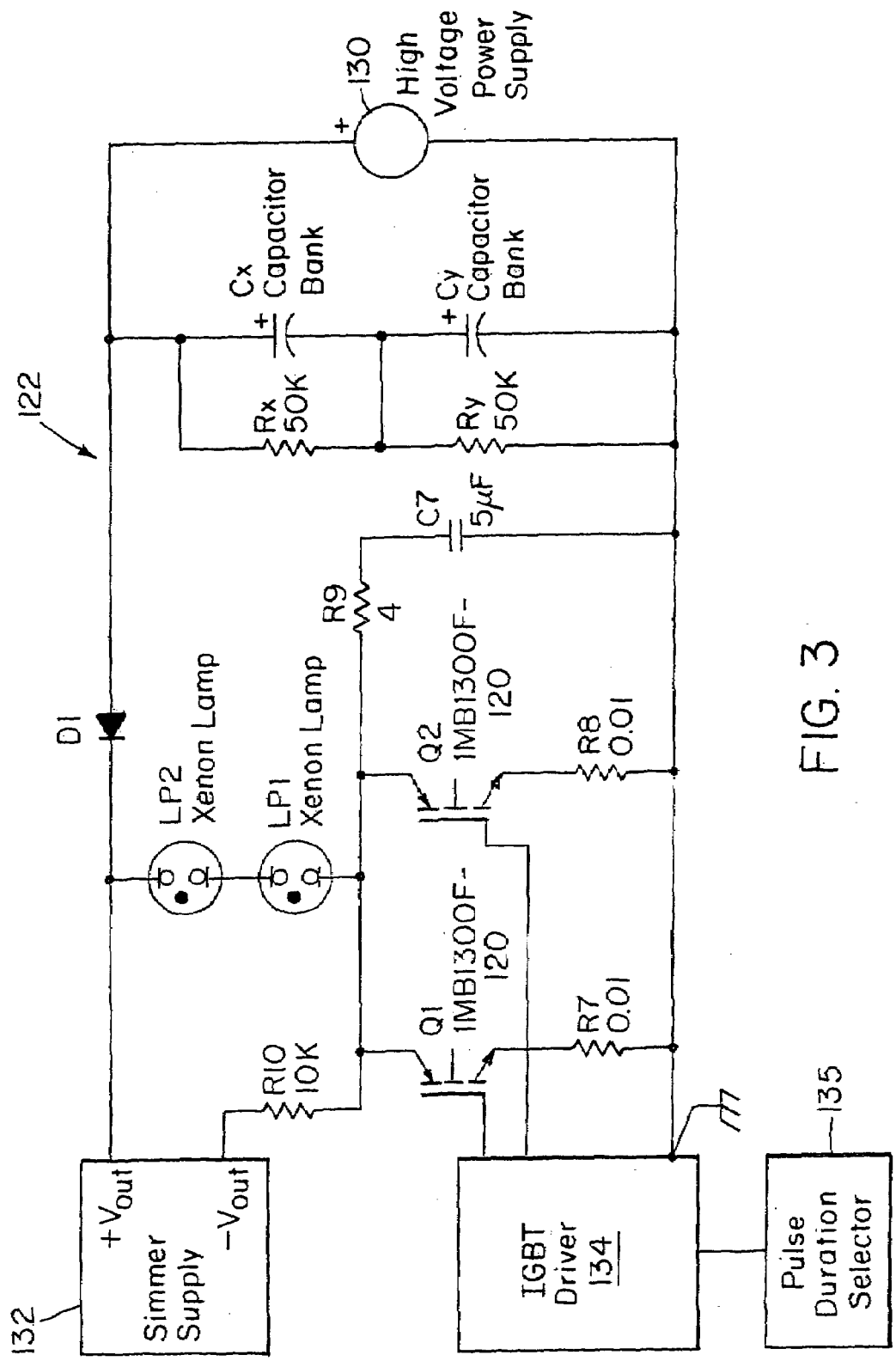
FIG. 3 is a circuit diagram showing an inventive flashlamp driver for the laser system.

FIG. 3 is a circuit diagram showing the flashlamp driver 122. Generally, the circuit has a simmer power supply 132 and a high voltage power supply 130 for two Xenon flashlamps, LP1 and LP2. As is known, the simmer supply 132 maintains the flashlamps LP1, LP2 at an operational temperature, so that when they are driven by the high voltage power supply, the light generation is near instantaneous. Two series capacitor banks, Cx, Cy, with parallel resistors Rx and Ry, respectively, are charged by the high voltage power supply to supplement the power provided to the flashlamps LP1, LP2 when pumping the alexandrite. With 1% efficient lasers at an output to 50 J, the excitation energy to the flashlamps must be approximately 5 kJ. This can be achieved with flashlamps of lengths of up to 10 cm.

Conventionally, laser flashlamps are driven by the high voltage power supply through a passive pulse-forming network (PFN). The present invention replaces this analog-style network with two IGBT transistors Q1,Q2 in an active PFN configuration. The IGBT power switches are unlike SCR or thyristors, which can only turn on large currents; the IGBT can turn off large currents. When large targets are used, the pulse durations needed are 5 to 50 msec. In operation, these transistors are normally in a non-conducting state. This connects the flashlamps, LP1 and LP2, only across the simmer power supply 132. When an IGBT driver 134, however, is signaled to initiate the generation of the laser light pulse, trigger signals are sent to both transistors Q1, Q2. This connects the series connected Xenon flashlamps LP1,LP2 to ground through resistors R7 and R8 and across the high voltage power supply 130. The flashlamps then draw current from both the high voltage power supply and the series capacitor banks Cx and Cy. In the present invention, the capacitor banks Cx and Cy are preferably constructed from low cost, compact electrolytic capacitors. For flashlamp lengths of up to 10 centimeters, the voltage required to drive the flashlamps at the required current to reach laser thresholds with long pulses is between 450 and 900 volts. Standard electrolytic capacitors are rated at 450 VDC, and series combinations can be used for higher voltages.

The use of transistors Q1,Q2 to connect the flashlamps across the high voltage power supply 130 has a number of advantages relative to prior art passive PFN circuits. First, with a passive PFN, it is generally difficult to provide for selection of the pulse duration; passive pulse-forming networks are generally tuned only to generate a pulse of a single duration. In contrast, the trigger pulse provided to the IGBT transistors Q1,Q2 may be easily digitally controlled via the IGBT driver 134, allowing any desired pulse duration consistent with the laser's characteristics and power supply. This is illustrated by the pulse duration selector 135 that preferably enables the operator to select pulse durations of 5, 10, or 20 msec. The only limitation on the pulse is the current the transistors Q1 and Q2 can conduct before they begin to be damaged. This factor, however, does not provide a hard upper limit to the pulse duration generated by the network since two or more transistors may be connected in parallel to meet the electrical current demands.

Figure 4A:
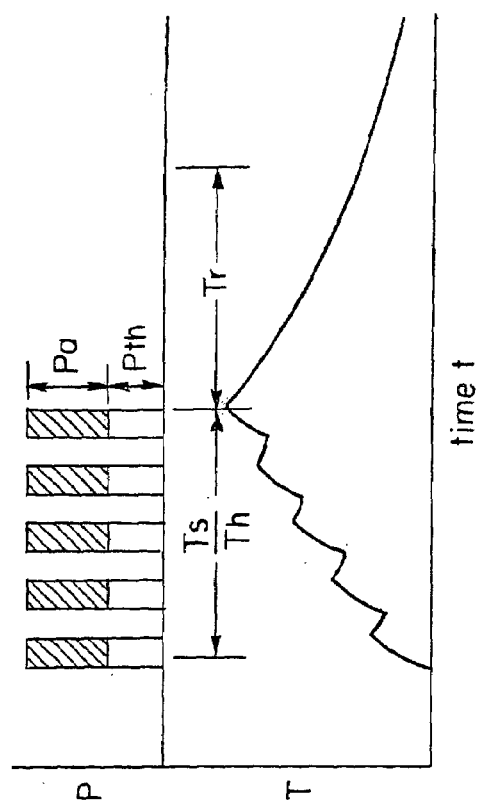
FIGS. 4A and 4B are plots of power/induced temperature as a function of time for pulse periodic heating and constant amplitude heating, respectively.

Further, the use of the active PFN additionally allows for the use of pulse periodic heating techniques. FIG. 4A is a plot of the power (P) supplied to the laser and the resulting temperature (T) of the targeted vessel as a function of time. A series of short subpulses are generated, with a fractional duty cycle over the selected effective pulse duration Ts by controlling transistors Q1 and Q2. Each subpulse has a duration of 1, 2, or 3 msec.

Figure 4B:
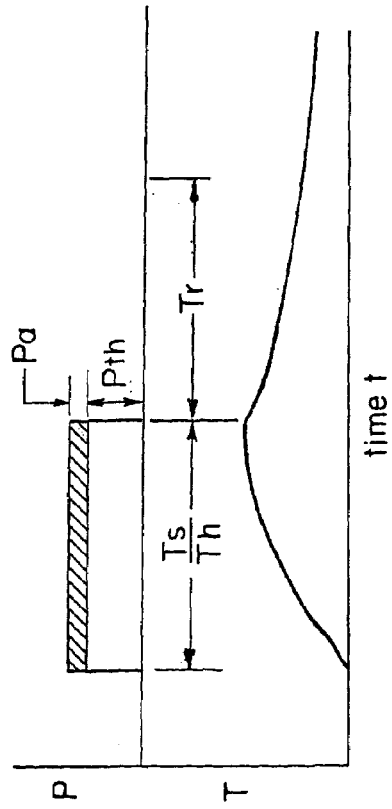

Pulse periodic heating techniques have certain advantages over constant amplitude heating shown in FIG. 4B, especially in flashlamp-excited lasers. A certain threshold of pump power Pth is needed to begin lasing in the gain media, the alexandrite. The excess flashlamp power Pa over this lasing threshold then determines the amplitude of the laser output beam. By compressing the generated light into a series of shorter pulses, a higher percentage of the pumping power used to excite the media is realized in the power of the output beam as shown by hatched regions in FIG. 4A. In contrast, as shown in FIG. 4B, when operating the laser in a constant amplitude mode, most of the power is consumed in reaching the lasing threshold. This power is lost to heat, increasing the need for liquid cooling and the demands on the power supply.

Generating the output laser light in a series of short pulses rather than a long steady-state pulse can greatly increase the efficiency of the laser for the same pump energy input. In such a scheme, to a first approximation where the effect of optimum output coupling on threshold is neglected, a gain in efficiency of as much as two-times can be achieved if the duty cycle of the multiple-pulse laser is less than 50%. Gains substantially higher can be made with an even lower duty cycle.

As also shown in FIGS. 4A and 4B, the temperature rise T induced in targeted structures within the dermal specimen by the pulse periodic heating is only slightly different than that induced by the continuous amplitude heating. The tissue temperature increases in a stepwise fashion with pulse periodic heating as opposed to gradually in the continuous amplitude case. This difference in heating, however, does not affect the efficacy of the therapy because it is only the maximum temperatures that determine whether or not the structures are destroyed.

There is a penalty to pay when time delay between sub-pulses is increased, however. If the inter-pulse delay becomes large enough, the pulses will behave independently.

According to one aspect, the periodicity of the sub-pulses is less than the thermal relaxation time of the targeted structures.

From a clinical standpoint, pulse periodic heating possesses certain advantages over constant-amplitude heating. The pulse width and pulse separation of the sub-pulses can be used to control the size of the targets to be heated and the maximum temperature to be reached. For smaller structures within the irradiation area that do not require treatment (including smaller normal-sized blood vessels), the inter-pulse delay time between consecutive sub-pulses should be greater than the thermal relaxation time of these structures, since pulses with pulses with separation longer than the thermal relaxation time do not have additive heating effect.

Pulse periodic heating may be applied for the treatment of vascular lesions where the target is blood vessels, including vessels larger than 30 microns in diameter.

The effective pulse duration of the envelope of laser pulses may be greater than 0.1, 0.5, 5, or 50 msec.

The laser can be a dye laser, solid-state laser, or gas-discharge laser.

With shorter pulse durations the advantages of pulse periodic heating techniques relative to constant amplitude heat become less pronounced. Generally, in the context of the inventive alexandrite laser system, pulse periodic heat is only required for effective pulse durations of greater than 10 msec.

1. Hair Removal Method

The alexandrite laser system has applications in cosmetic, i.e., non-therapeutic, hair removal. The use of alexandrite is preferred to other laser systems for a number of reasons. Alexandrite is tunable through a 100 nm range surrounding 760 nm. This range has a number of advantages relative to ruby or pulsed dye lasers that have been used in the past.

Figure 5:
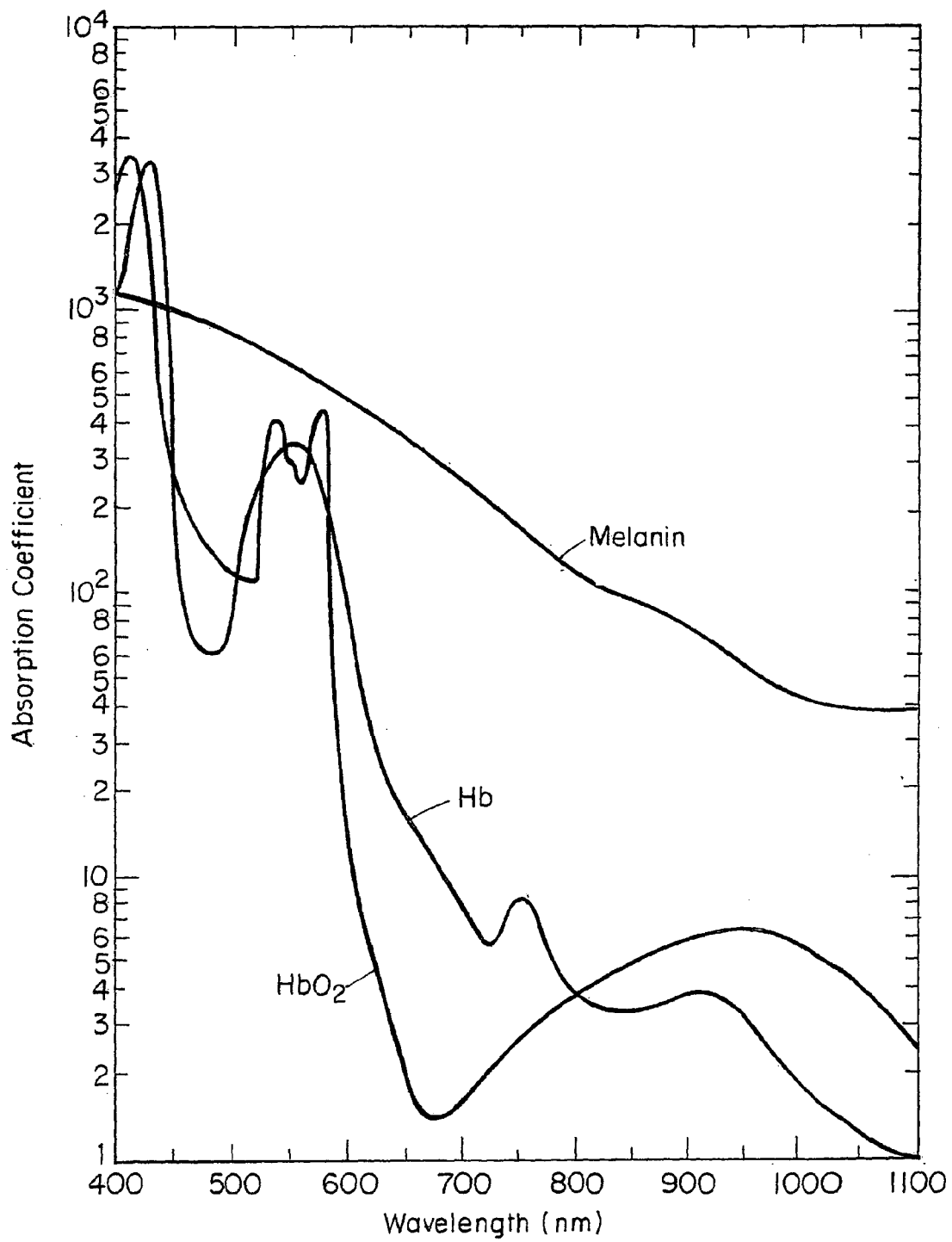
FIG. 5 is a plot of the spectral absorption of hemoglobin and melanin.

Pulsed dye lasers operating in the 577–585 nm range are well absorbed by the deoxy-hemoglobin (Hb) and oxy-hemoglobin (HbO$_2$) relative to the melanin, as shown in FIG. 5. This provides good selectivity. The problem, however, is that the total absorption of the melanin is very high. As a result, the laser light does not penetrate very deeply into the dermal layer. To effectively render inactive the hair-producing skin structures, the light must penetrate deeply, up to 5 millimeters, to the hair papilla and the nutrient blood vessels that surround it.

Ruby lasers operating at 694 nm do achieve good penetration since the absorption of melanin is incrementally lower at this wavelength. The problem here, however, is that the Hb and HbO$_2$ have low absorptions at this wavelength, as also shown in FIG. 5. To effectively and permanently stop the growth of a hair, the light must penetrate down to the papilla and be absorbed in the papilla but also the surrounding nutrient blood vessels. Ruby lasers do not achieve this destruction because of their poor blood absorption. This is why the prior art teaches the use of exogenous absorbers. These absorbers, however, do not solve the problem since they do not reach to the depth of the papilla.

In contrast, in the 50 nm range surrounding 755 nm, where the inventive alexandrite laser system operates, melanin absorption is lower, compared to the ruby laser. Thus, better penetration is achieved down to the hair's papilla to the approximately five millimeter depth. Somewhat more importantly, however, is the fact that the absorption of Hb peaks in this range and the absorption of HbO$_2$ is substantially higher than at the ruby laser's wavelength. These factors combine to allow laser light to 1) penetrate to the depth of the papilla and blood vessels supplying the papilla; and 2) then be absorbed by the melanin, and hemoglobin containing blood cells in those vessels. Because of the long pulse durations, blood in small vessels between the surface of the skin and the papilla diffuse its heat to surrounding tissue and is not heated to denaturation. Blood in the papilla is heated because the heat is confined within the papilla which is a large structure.

A further advantage relative to other lasers is the fact that alexandrite lasers without a Q-switching element can generally allow longer pulse durations than dye lasers. This factor is relevant because the pulse duration of the irradiating light is important for selectivity. If the pulse duration is too long, the heat absorbed by the papilla and surrounding vessels would diffuse into the surrounding dermal tissue so that the papilla and blood vessels would not be selectively heated to the degree necessary to destroy only those structures. If the pulse durations are too short, however, the smaller light absorbing chemical species, such as the blood hemoglobin or melanin, and smaller blood vessels will not be cooled by heat diffusion and the epidermis will be overheated and burn. This effect can cause purpura, bleeding, and burning but also generally is not effective at permanently stopping hair growth. This is why the shorter pulse duration ruby lasers only find limited success in permanently removing the hair.

In the preferred embodiment, the laser system irradiates the treated skin section with laser light output pulses having durations of between 1 and 40 msec for hair removal. The best results, however, have been achieved using pulses of approximately 5 to 10 msec or longer.

Use of the long pulse alexandrite laser also has certain advantages relative to other alexandrite laser systems used in the prior art for tattoo removal and pigmented lesion treatment. Historically, alexandrite lasers generally have been viewed as difficult to implement. The Q-switching element in the laser cavity made operation of the laser unstable. In the present laser system, the Q-switching element is removed and the gain medium laser is driven into the longer pulse durations. This improves the operation of the laser.

The invention additionally, preferably includes the use one or more topical applications on the skin to be treated. Mineral oil, K-Y® jelly or any other wet, penetrating, biocompatable application is preferably applied in a layer over the hair-bearing skin that is to be then laser treated. The layer provides gross refractive index-matching.

In addition to the index-matching layer, a thermo- or photo-sensitive irradiation marker is included as a separate layer to the index-matching layer or in a common vehicle with the index-matching substance. This thermochromic or photochromic marker preferably changes color or state in response to being exposed by the laser light output pulse. This indicates to the operator those portions of the skin surface that have been exposed. The marker may be a temperature indicating crayon or liquid that liquefies at a known temperature, such as sold commercially by Omega Engineering, Inc., although bio-compatibility has not yet been confirmed with these products.

The use of a thermochromic or a photochromic marker is useful when irradiating the skin with light in the near-infrared. When skin is exposed to pulsed light in the shorter frequencies, such as 577–585 nm, there is an instantaneous purpuric effect which acts as a record of those portions of the skin that have been treated. This effect does not occur when the skin is irradiated with the near-infrared. Use of the marker which changes color or state, for example, in response to the light or indicated heat, however, provides the helpful indication of those portions of the skin that have been treated.

Figure 6:
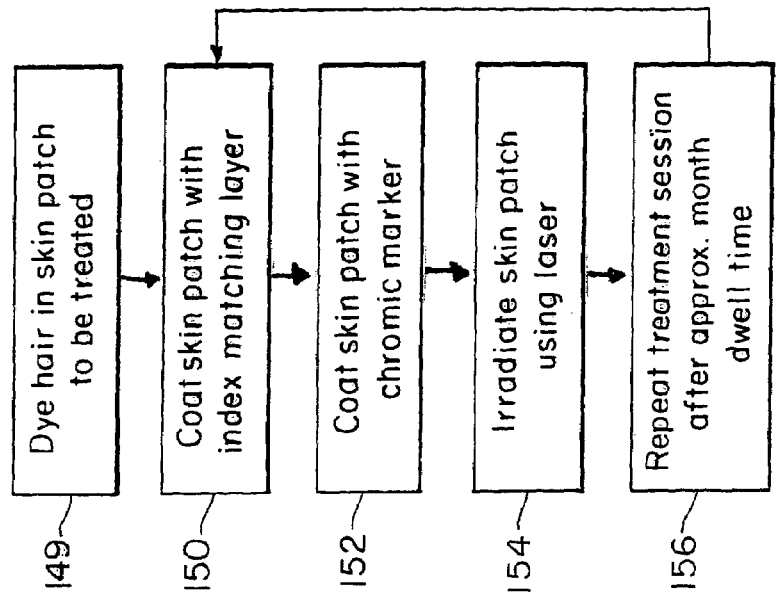
FIG. 6 is a process diagram showing hair removal according to the invention.

FIG. 6 is a method diagram showing the inventive hair removal technique using the alexandrite laser.

As a preliminary step 149, it may be helpful to have some patients first dye the hair in the skin patch containing unwanted hair. This is especially helpful for those patients having light-colored hair. The hair coloring is perform with any dark-colored commercially available hair dye. It is preferably performed by the patient in the days proceeding the laser treatment. As with these commercially hair dyes, the dyeing effect penetrates deeply into the hair shaft in the follicle to the papilla. This facilitates the absorption of the laser energy into the hair producing structures in the papilla and surrounding it, which increases selectivity.

The skin patch to be treated is first coated with the index-matching layer in step 150. The thermochromic or photochromic marker is also be coated over the skin patch in step 152 possibly with the index-matching layer.

The skin patch is then irradiated with the laser light pulse in step 154. The entire surface of the skin patch is preferably irradiated with about 20 J/cm$^2$ using separate or slightly overlapping spots on the skin. The spots are located on the skin to ensure treatment of each follicle. The number of laser light pulses needed to irradiate the skin during each application depends upon the spot size, which depends on the laser's power. A higher powered laser can achieve the 20 J/cm$^2$ of energy necessary in the 5 msec pulse duration and thus can use a larger spot size. Seven millimeters spot size represents a good trade-off between laser power available under a current technology and a spot size that is large enough to efficiently treat the areas in a reasonably time. The thermochromic or photochromic marker indicates to the operator those parts of the skin that already have been treated.

Medical experiments have suggested that better results occur if the skin patch is irradiated only once in the same treatment session. Preferably, each section of the patch should receive one 5 msec laser light pulse providing a fluence of 20 j/cm$^2$.

This protocol then is repeated after approximately month long intervening dwell intervals in step 156. Generally, the first session is not entirely successful at removing all of the hair. Those follicles that do not contain a hair shaft generally are insufficiently irradiated to terminate any future hair growth. The absence of the added absorption of the hair shaft results in lower temperatures than that necessary to sufficiently damage the hair producing structures. During the first irradiation, most of the hair follicles that contain hair are destroyed. Then, across the intervening dwell interval, those follicles that previously did not have hairs grow their own hairs so that when treatment again is performed those hair follicles showing new growth are destroyed. For complete hair removal, this process generally must be repeated three or four times with the hair re-dyeing of step 149 repeated as necessary.

2. Method for Treatment of Unwanted Veins

The alexandrite laser system may also be used for the cosmetic, i.e., non-therapeutic, treatment of unwanted veins. Varicose and telangiectatic leg veins are common forms of ectatic vascularization. Varicose veins have been classified into three groups: dilated saphenous veins, dilated superficial branches and dilated venules. More encompassing classification for the conditions is simply unwanted leg veins. Light therapy, sclerotherapy, and vein stripping are typical modes of treating these conditions. Each therapy has its advantages and disadvantages. In the present invention light therapy and sclerotherapy are combined to achieve results and success rate unattainable by the therapies alone.

FIG. 7A shows a combined light and sclerotherapy technique implementing the principles of the present invention. Generally, the technique includes near-infrared irradiation of the targeted vessels preferably using the alexandrite laser followed by a dwell time in which the destructive effects of the light therapy are realized in the targeted vessels. After this time expires, sclerotherapy is performed on the vessels. Alternatively, the sclerotherapy could be performed first followed by the dwell time and then the near-infrared irradiation of the unwanted vessels as shown in FIG. 7B and discussed later.

In more detail, light therapy is first performed in steps 310–316. The first step in this process, step 310, is to assess the size and depth of the targeted varicose or telangiectatic leg veins. Generally an experienced physician can do this visually, although measuring devices may be used.

The size of the targeted vessels dictates the effective pulse duration and total fluence, in step 312. The pulse duration should ideally be closely matched to the thermal relaxation time of the vessels, and the thermal relaxation time is a function of the vessels size. Generally, for the treatment of the vessels such as varicose veins, total effective pulse durations of greater than a millisecond are desirable, with 5 milliseconds to 100 milliseconds being preferred in the case of larger vessels.

The total fluence is dictated also by the vessel's size. The fluence should be high enough to, over the course of the pulse duration, raise the walls of the vessel to a temperature at which their constituent proteins will denature. A temperature of 70° C. is an accepted target. In general, the total energy deposited is preferably greater than 5 J/cm$^2$, although fluences in the range of 15–30 J/cm$^2$ are more common with approximately 20 J/cm$^2$ preferred in most situations.

In step 314, the wavelength of the irradiating light is selected based upon the depth and size of the vessels. Generally, for smaller telangiectatic veins near the skin's surface, the desired wavelength is 577–585 nanometers. The limited penetration depth at this wavelength is not a substantial impediment, and the high selectivity is desirable. For deeper lying and/or larger vessels, however, the near-infrared is the desirable wavelength. Deeper-lying vessels require wavelengths that are less efficiently absorbed by the dermis and epidermis. The light can penetrate to the depth of the vessels without being absorbed by melanin. Vessels having larger cross-sections also require near-infrared for more even cross-sectional heating. FIG. 4 shows that alexandrite laser light at 755 nm is better matched to absorption by both hemoglobin and oxy-hemoglobin than the common ruby laser light at 694 nm.

Figure 8:
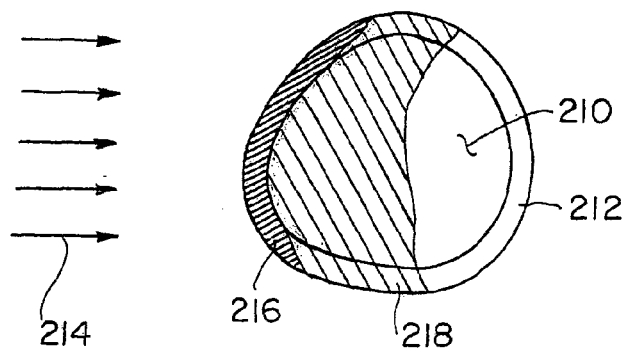
FIG. 8 shows a blood vessel cross-section and the different heating effects that are gained by using 577–585 nanometer light as opposed to near-infrared light.

FIG. 8 shows a blood vessel cross-section with an interior of the lumen 210 surrounded by the lumen's wall 212. For incident light indicated by arrows 214, the 577–585 nanometer range will be generally absorbed in a small region of the vessel's directly exposed wall (see reference numeral 216). For the larger vessels shown, this limits the area where the destructive effects of the light are realized. In contrast, when less efficiently absorbed near-infrared light is used, the region of heating 218 is expanded to cover a larger percentage of the interior 210 and also more of the vessel's walls 212. For larger vessels, this enlarged area is desirable. Specifically, the preferred light source is an alexandrite laser operating in the 755 nm range. Although, an alexandrite laser operating anywhere within its operational range of 710 to 810 nanometers could achieve some success. Filtered flashlamp light sources are also possible as are ruby, semiconductor diode, titanium-doped crystal, and Nd-doped crystal.

Returning to FIG. 7A, prior to irradiation, a thermal- or photo-sensitive irradiation marker is covered over the skin patch that is to be irradiated and that contains the unwanted vessels in step 315. This marker indicates to the operator those portions of the skin that have been exposed. The marker can be a temperature indicating liquid or stick that melts upon exposure to laser or the heat generated by it. One example is, OMEGALAQ™ produced by Omega Engineering, Incorporated although the bio-compatibility of this product has not been confirmed.

The use of a thermochromic or photochromic marker is useful when irradiating the skin with light in the near-infrared. When skin is exposed to light in the shorter frequencies, such as 577–585 nm, there is an instantaneous skin color change that acts as a record of those portions of the skin that have been treated. This effect does not occur when the skin is irradiated with the near-infrared. The use of the marker, which changes color or state for example in response to the light or induced heat, provides the helpful indication of those portions of the skin that have been treated.

The dermis containing the unwanted vessels is then irradiated using the selected wavelength, effective pulse duration, and fluence in step 316. Although a constant or near constant amplitude pulses may be used, the present invention preferably relies on pulse periodic heating techniques for longer pulse durations.

The next step (318) is a waiting period or dwell time after the light therapy. This can be as short as 12 hours or as long as 6 months. The reason why this dwell time is necessary is not clear. It is theorized that this time allows the destructive effects of the light therapy to mature in the targeted vessels.

Finally, sclerotherapy is performed in step 320 on the vessels after the expiration of the dwell time. This is performed according to commonly known techniques in which a sclerosing agent is injected into the vessels. Preferred sclerosing agents include hypertonic saline and dextrose or and polidocanol (also known as Aetoxisclerol™). Lidocaine or other local anesthetic may be added to any of these solutions to assist in pain control. This is discussed in detail in *Sclerotherapy*, which is incorporated herein in its entirety by this reference.

FIG. 7B shows another embodiment of the combined light and sclerotherapy technique of the present invention. The second embodiment is similar to the technique disclosed in FIG. 7A insofar as the irradiation steps of 310–316 correspond to the irradiation steps of 326–334 in FIG. 7B. The second embodiment also implements a dwell time 324 and sclerotherapy is step 322. The difference here, however, is that the sclerotherapy 322 is performed before the irradiation in steps 326–334. The dwell time, step 324 follows the sclerotherapy 322 and then the irradiation 326–334.

The laser system may be sold as part of a kit that includes an instruction manual that advises the combination of sclerotherapy with laser irradiation as shown in FIGS. 7A and 7B. The kit may also include the marker that shows were irradiation has been performed along with a sclerosing agent.

Experimental Results for the Combined Light Therapy and Sclerotherapy

A number of patients were treated first with a laser generating 5 msec pulses at 755 nm and then with sclerotherapy according to the following general protocol.

The area to be treated was identified and a template was placed to accommodate the group of veins to be treated in such a fashion that they could be easily identified. Anatomic landmarks and skin lesions were marked on the template so that placement could be accurately reproduced. Six punchouts were then marked with a skin marking pen to "index" the photograph and the treatment cites. Two baseline photographs were taken. Sites were then treated with either 1) 15.0 J/cm$^2$, single pulse; 2) 15 J/cm$^2$, double pulse; 3) 20 J/cm$^2$, single pulse; 4) 20 J/cm$^2$, double pulse; and 30 J/cm$^2$, single pulse of radiation from the laser. After this treatment was performed, the patient was given a follow-up appointment in approximately 4 weeks.

At the second appointment, templates were again applied to the treatment site; the landmarks were matched; and the index marking holes were marked as well. Photographs were taken using the same protocol as in the first treatment session. The areas were again retreated using 20 J/cm$^2$ in a single or double pulse.

Some of the patients were treated again for a third time after another four week interval. This treatment was performed with the same protocol, in each case 20 J/cm$^2$ in two pulses was used.

In all the patients, sclerotherapy was performed within approximately 4 weeks from the last light-based therapy. In each case, 4–7 cc of 23.4% sterile, unpreserved saline solution mixed 30:1 with 2% Xylocaine was injected using a 30 gauge needle with a loupe assisted vision into any remaining spider veins.

Figure 9:
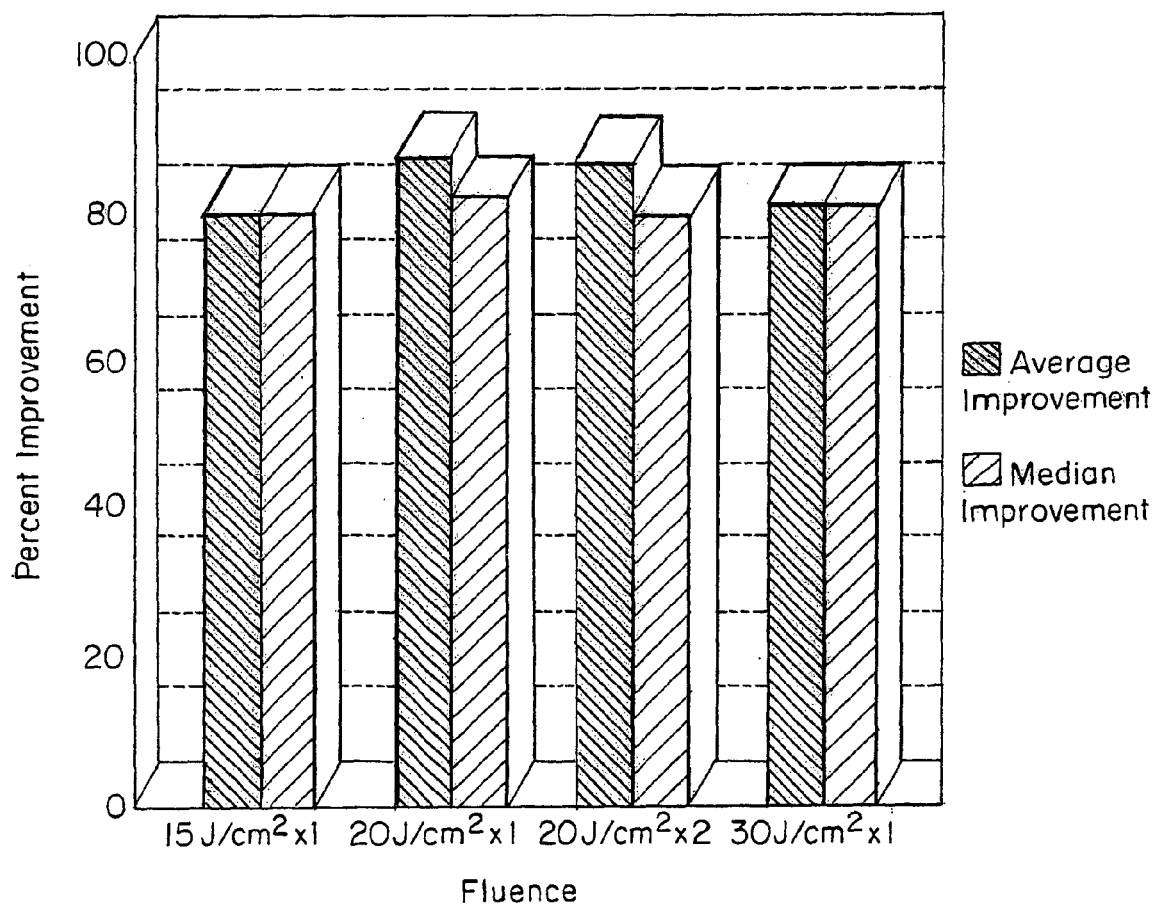
FIG. 9 is a graph illustrating the percent of leg vein elimination for various combinations of fluences and pulse combinations.

The general results of the limited study was that most patients showed greater than 76% clearing, with some patients exhibiting almost complete resolution of the veins. FIG. 9 summarizes the results for a number of different fluences included in the experiment, specifically 15 J/cm$^2$ single pulse, 20 J/cm$^2$ single pulse, 20 J/cm$^2$ double pulse, and 30 J/cm$^2$ single pulse. In each case, the average and median improvement exceeded 80%.

While this invention has been particularly shown and described with references to preferred embodiments thereof, it will be understood by those skilled in the art that various changes in form and detail may be made therein without departing from the spirit and scope of the invention as defined by the appended claims.

What is claimed is:

1. A method for wearing biologic tissue with pulse light, comprising:
   generating a long effective output light pulse comprising a series of sub-pulses having a fractional duty cycle over a selected effective pulse duration, a periodicity that is less than the thermal relaxation time of a targeted structure, and an interpulse-delay between successive sub-pulses that is greater than the thermal relaxation time of non-targeted structures within the treatment area, the targeted structures being substantially adjacent to the non-targeted structures within the treatment area; and delivering the output light to the tissue of a patient.

2. The method as described in claim 1 wherein the output light pulse comprises a laser light pulse.

3. The method as described in claim 1 wherein the effective pulse duration is approximately equal to the thermal relaxation time of the targeted structure.

4. The method as described in claim 1 wherein the targeted structure comprises blood vessels.

5. The method as described in claim 4 wherein the targeted blood vessels are larger than 30 microns in diameter.

6. The method as described in claim 1 wherein the effective pulse duration is larger than 0.1 msec.

7. The method as described in claim 1 wherein the effective pulse duration is larger than 0.5 msec.

8. The method as described in claim 1 wherein the effective pulse duration is larger than 5 msec.

9. The method as described in claim 1 wherein the effective pulse duration is larger than 50 msec.

10. The method as described in claim 1 wherein the non-targeted structures include nonnal-sized blood-vessels.

* * * * *

UNITED STATES PATENT AND TRADEMARK OFFICE
CERTIFICATE OF CORRECTION

PATENT NO. : 7,118,562 B2  Page 1 of 1
APPLICATION NO. : 10/631213
DATED : October 10, 2006
INVENTOR(S) : Horace W. Furumoto It is certified that error appears in the above-identified patent and that said Letters Patent is hereby corrected as shown below:

Claim 1, column 14, line 63, delete "wearing" and insert --treating--
Claim 10, column 16, line 13, delete "nonnal" and insert --normal--

Signed and Sealed this

Second Day of January, 2007

JON W. DUDAS
*Director of the United States Patent and Trademark Office*

UNITED STATES PATENT AND TRADEMARK OFFICE
CERTIFICATE OF CORRECTION

PATENT NO. : 7,118,562 B2
APPLICATION NO. : 10/631213
DATED : October 10, 2006
INVENTOR(S) : Horace W. Furumoto Page 1 of 1

It is certified that error appears in the above-identified patent and that said Letters Patent is hereby corrected as shown below:

Claim 1, column 14, line 63, delete "wearing" and insert --treating--
Claim 10, column 16, line 13, delete "nonnal" and insert --normal--

Signed and Sealed this

Thirtieth Day of January, 2007

JON W. DUDAS
*Director of the United States Patent and Trademark Office*